United States Patent [19]

Gasson et al.

[11] Patent Number: 4,918,067
[45] Date of Patent: Apr. 17, 1990

[54] HETEROCYCLIC SUBSTITUTED PENICILLIN ANTIBIOTICS

[75] Inventors: Brian C. Gasson; Michael J. Pearson, both of Brockham Park, England

[73] Assignee: Beecham Group p.l.c., United Kingdom

[21] Appl. No.: 76,360

[22] Filed: Jul. 22, 1987

[30] Foreign Application Priority Data

Jul. 24, 1986 [GB] United Kingdom ................ 8618094
Apr. 16, 1987 [GB] United Kingdom ................ 8709258
Apr. 16, 1987 [GB] United Kingdom ................ 8709259

[51] Int. Cl.$^4$ .................. A61K 31/43; C07D 499/46; C07D 239/02; C07D 213/53; C07D 285/08
[52] U.S. Cl. .................................... 514/196; 514/195; 540/316; 540/328; 540/335; 544/332; 546/311; 546/312; 546/338; 548/128
[58] Field of Search ................ 540/316, 328, 335; 514/195, 196; 544/332; 548/128; 546/311, 312, 338

[56] References Cited

U.S. PATENT DOCUMENTS

| | | | |
|---|---|---|---|
| 3,932,385 | 1/1976 | Cook | 540/328 |
| 3,936,443 | 2/1976 | Gregson et al. | 540/335 |
| 3,991,046 | 11/1976 | Gregson et al. | 540/335 |
| 4,394,384 | 7/1983 | Takaya et al. | 540/225 X |
| 4,692,518 | 9/1987 | Lord | 540/224 |

FOREIGN PATENT DOCUMENTS 0074268 3/1983 European Pat. Off. .
1051723 12/1966 United Kingdom .

OTHER PUBLICATIONS

Chemical Abstracts, vol. 83: 147474e (1975).
Chemical Abstracts, vol. 107: 217358k (1987).

Primary Examiner—Werren B. Lone
Assistant Examiner—Vera C. Clarke
Attorney, Agent, or Firm—Jacobs & Jacobs

[57] ABSTRACT

The present invention provides a compound of formula (I) or a pharmaceutically acceptable salt or in-vivo hydrolysable ester thereof:

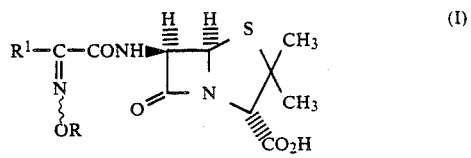

wherein $R^1$ is a 5 or 6 membered sulphur and/or nitrogen containing heterocyclic group substituted by an optionally protected amino group, with the proviso that $R^1$ is not 2-aminothiazol-4-yl, and R is hydrogen; optionally substituted $C_{1-12}$ alkyl; optionally substituted $C_{2-12}$ alkenyl or alkynyl; carbocyclyl; aryl or heterocyclyl.

These compounds have antibacterial properties, and therefore are of use in the treatment of bacterial infections in humans and animals caused by a wide range of organizations.

25 Claims, No Drawings

HETEROCYCLIC SUBSTITUTED PENICILLIN ANTIBIOTICS

This invention relates to novel β-lactam containing compounds, their preparation and their use, and in particular to a novel class of penicillins. These compounds have antibacterial properties, and therefore are of use in the treatment of bacterial infections in humans and animals caused by a wide range of organisms.

British Patent Specification No. 1 399 087 discloses a novel class of penicillin antibiotics containing a 6β-(α-etherified oxyimino)-acylamino group.

The present invention provides a compound of formula (I) or a pharmaceutically acceptable salt or in-vivo hydrolysable ester thereof:

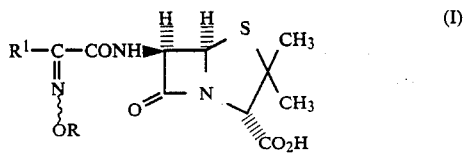

wherein $R^1$ is a 5 or 6 membered sulphur and/or nitrogen containing heterocyclic group substituted by an optionally protected amino group, with the proviso that $R^1$ is not 2-aminothiazol-4-yl, and R is hydrogen; optionally substituted $C_{1-12}$ alkyl; optionally substituted $C_{2-12}$ alkenyl or alkynyl; carbocyclyl; aryl or heterocyclyl.

Preferably $R^1$ is a 5 or 6 membered heterocycle containing 1 or 2 nitrogen atoms and optionally one sulphur atom.

Preferably $R^1$ will include one of the following groups: aminopyridyl, aminopyrimidyl or aminothiadiazolyl.

Substituents that may be present on those groups R defined hereinabove as being optionally substituted include carboxyl, esterified carboxy, carbonyl, hydroxy, alkoxy, cyano, carbamoyl, N-substituted carbamoyl, aryloxy, aralkoxy, mercapto, alkylthio, arylthio, amino, substituted amino, halo, nitro, azido, formyl, acyl, acyloxy, phthalimido, acylamino, alkoxycarbonylamino, aralkoxy-carbonylamino, aryl, heterocyclyl and carbocyclyl.

When R is substituted methyl, the preferred substituents are carbocyclyl, aryl, heterocyclyl, cyano, carboxyl, esterified carboxy, carbamoyl and N-substituted carbamoyl, alkylthio, arylthio and halo.

Suitable $C_{1-12}$ alkyl groups include straight and branched chain alkyl groups containing 1 to 12 carbon atoms. Preferred alkyl groups contain 2 to 6 carbon atoms, such as t-butyl.

Suitable $C_{2-12}$ alkenyl groups include straight and branched chain alkenyl groups containing 2 to 12 carbon atoms. Preferred alkenyl groups contain 2 to 6 carbon atoms, such as propenyl and butenyl.

Suitable $C_{2-12}$ alkynyl groups include straight and branched chain alkynyl groups containing 2 to 12 carbon atoms. Preferred alkynyl groups contain 2 to 6 carbon atoms such as propynyl and butynyl.

The term "carbocyclyl" herein denotes single or fused aromatic or partly or wholly saturated carbocyclic rings, optionally substituted with one or more groups, which may be the same or different, selected from optionally substituted $C_{1-6}$ alkyl, optionally substituted $C_{2-6}$ alkenyl, optionally substituted $C_{2-6}$ alkynyl, optionally substituted exo-methylene, carboxyl, $C_{1-6}$ alkoxycarbonyl, oxo, hydroxy, alkoxyimino, oxyimino, $C_{1-6}$ alkoxy, cyano, carbamoyl, N-substituted carbamoyl, aryloxy, aralkoxy, mercapto, alkylthio, arylthio, amino, substituted amino, halo, nitro, azido, formyl, acyl, acyloxy, phthalimido, acylamino, alkoxycarbonylamino, aralkoxy-carbonylamino, aryl, heterocyclyl and carbocyclyl. Suitable substituents for $C_{1-6}$ alkyl, $C_{2-6}$ alkenyl, $C_{2-6}$ alkynyl and exo-methylene include those referred to above as substituents for R. Preferably the carbocyclic system comprises between one and four rings, attached via a non-aromatic ring carbon atom thereof.

Suitable carbocyclyl groups include optionally substituted $C_{3-12}$, preferably $C_{4-8}$, cycloalkyl; optionally substituted $C_{6-12}$, preferably $C_{7-10}$, bicycloalkyl; optionally substituted $C_{7-14}$, preferably $C_{9-12}$, tricycloalkyl; optionally substituted $C_{7-14}$, preferably $C_{10-14}$, tetracycloalkyl; optionally substituted $C_{4-12}$, preferably $C_{5-8}$, cycloalkenyl; optionally substituted $C_{6-12}$, preferably $C_{7-10}$, bicycloalkenyl; and optionally substituted $C_{8-14}$, preferably $C_{10-14}$, tricycloalkenyl. Examples of carbocyclyl groups include indan 2-yl.

Suitable $C_{3-12}$ cycloalkyl groups include cyclopentyl, cyclohexyl, cycloheptyl and cyclooctyl.

Suitable $C_{6-12}$ bicycloalkyl groups include bicyclo [2.2.1]heptyl (norbornyl) and bicyclo[2.2.2]octyl.

Suitable $C_{4-12}$ cycloalkenyl groups include cyclopentenyl and cyclohexenyl.

Examples of $C_{6-12}$ bicycloalkenyl groups include 6,6-dimethylbicyclo[3.1.1]hept-2-en-yl, and 5-norbornen-2-yl.

Suitable $C_{7-14}$ tricycloalkyl groups include adamantyl.

Suitable $C_{7-14}$ tetracycloalkyl groups include tetracyclo [$7.2.1.0^{4,11}.0^{6,10}$] dodecanyl.

Suitable $C_{8-14}$ tricycloalkenyl groups include tricyclo [$6.2.1.0^{2,7}$] undec-4-enyl. Carbocyclyl, as defined herein, includes aryl. When used herein the term 'aryl' includes phenyl and naphthyl optionally substituted with up to five, preferably up to three, groups, which are the same or different, selected from halogen, optionally substituted $C_{1-6}$ alkyl, carbocyclyl, alkylthio, acylamino, phenyl, $C_{1-6}$ alkoxy, halo($C_{1-6}$) alkyl, hydroxy, amino, nitro, carboxy, carbamoyl, N-substituted carbamoyl, $C_{1-6}$ alkoxycarbonyl, $C_{1-6}$ alkoxycarbonyl-($C_{1-6}$)-alkyl, $C_{1-6}$ alkylcarbonyloxy, $C_{1-6}$ alkylcarbonyl or heterocyclyl groups.

The term "heterocyclyl" herein denotes single or fused aromatic or non-aromatic rings, at least one of which comprises up to four hetero atoms selected from oxygen, nitrogen and sulphur, each ring being optionally substituted with up to three groups, which are the same or different, selected from halogen, $C_{1-6}$ alkyl, carbocyclyl, alkylthio, acylamino, $C_{1-6}$ alkoxy, halo($C_{1-6}$)alkyl, hydroxy, amino, carboxy, carbamoyl, N-substituted carbamoyl, acyl, $C_{1-6}$ alkoxycarbonyl, $C_{1-6}$ alkoxycarbonyl($C_{1-6}$)alkyl, aryl or oxo groups.

Suitably at least one heterocyclic ring comprises from 4 to 7 ring atoms, preferably 5 or 6 atoms.

Particularly suitable heterocyclyl groups consist of a 5- or 6-membered heterocyclic ring containing from one to three heteroatoms selected from oxygen, nitrogen and sulphur and optionally substituted as set out above. Examples of heterocyclyl groups include tetrahydrothien-3-yl, and 1,1, dioxotetrahydrothien-3-yl.

The term 'halogen' refers to fluorine, chlorine, bromine and iodine.

Compounds of the invention may exist in two or more tautomeric forms, e.g. those having the partial structures below:

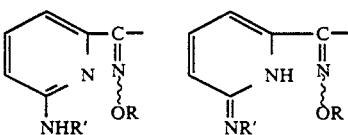

Further tautomeric forms may be present in the compounds wherein R is heterocyclyl. It should be understood that all tautomeric forms of the compound of formula (I) are included within the scope of the invention.

Suitable amino protecting groups are those well known in the art which may be removed under conventional conditions without disruption of the remainder of the molecule.

Examples of amino protecting groups include $C_{1-6}$ alkanoyl; benzoyl; benzyl optionally substituted in the phenyl ring by one or two substituents selected from $C_{1-4}$ alkyl, $C_{1-4}$ alkoxy, trifluoromethyl, halogen, or nitro; $C_{1-4}$ alkoxycarbonyl; benzyloxycarbonyl or trityl substituted as for benzyl above; allyloxycarbonyl, trichloroethoxycarbonyl or chloroacetyl.

Advantageously, R is joined to the oxyimino group through a secondary or tertiary carbon atom of R, more preferably a non-aromatic ring carbon atom of a carbocyclic system which may be multicyclic.

Particularly preferred values of R within the present invention are cyclopentyl, cyclohexyl and t-butyl.

The term "pharmaceutically acceptable salts" as used herein in respect of compounds of formula (I) includes both mono and di- salts formed at either or both of the carboxylic groups, one of which is attached to the penicillin nucleus and the other of which is present when R is substituted by carboxyl. Similarly the term "in-vivo hydrolysable ester" when used herein applies to both mono and di- esters.

Examples of suitable pharmaceutically acceptable in vivo hydrolysable ester groups include those which break down readily in the human body to leave the parent acid or its salt. Suitable ester groups of this type include those of part formula (i), (ii), (iii) and (iv):

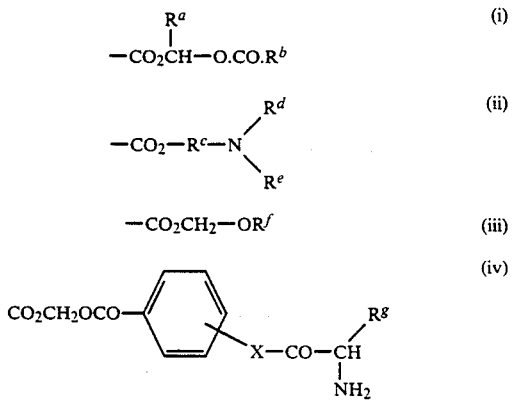

wherein $R^a$ is hydrogen, $C_{1-6}$ alkyl, $C_{3-7}$ cycloalkyl, methyl, or phenyl, $R^b$ is $C_{1-6}$ alkyl, $C_{1-6}$ alkoxy, phenyl, benzyl, $C_{3-7}$ cycloalkyl, $C_{1-6}$ alkyl $C_{3-7}$ cycloalkyl, 1-amino $C_{1-6}$ alkyl, or 1-($C_{1-6}$ alkyl)amino $C_{1-6}$ alkyl; or $R^a$ and $R^b$ together form a 1,2-phenylene group optionally substituted by one or two methoxy groups; $R^c$ represents $C_{1-6}$ alkylene optionally substituted with a methyl or ethyl group and $R^d$ and $R^e$ independently represent $C_{1-6}$ alkyl; $R^f$ represents $C_{1-6}$ alkyl; $R^g$ represents hydrogen or phenyl optionally substituted by up to three groups selected from halogen, $C_{1-6}$ alkyl, or $C_{1-6}$ alkoxy; and X is (preferably o) oxygen or (preferably o or p)NH.

Examples of suitable in vivo hydrolysable ester groups include, for example, acyloxyalkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; alkoxycarbonyloxyalkyl groups, such as ethoxycarbonyloxymethyl and α-ethoxycarbonyloxyethyl; dialkylaminoalkyl especially di-loweralkylamino alkyl groups such as dimethylaminomethyl, dimethylaminoethyl, diethylaminomethyl or diethylaminoethyl; lactone groups such as phthalidyl and dimethoxyphthalidyl; and esters linked to a second β-lactam antibiotic or to a β-lactamase inhibitor.

A further suitable pharmaceutically acceptable in vivo hydrolysable ester group is that of the formula:

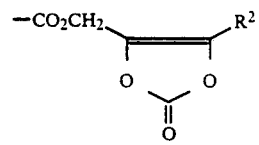

wherein $R^2$ is hydrogen, $C_{1-6}$ alkyl or phenyl.

The in-vivo hydrolysable esters of compounds of formula (I) are preferred where the antibiotic is for oral administration.

Suitable pharmaceutically acceptable salts of the carboxy group of the compound of formula (I) include metal salts, e.g. aluminum, alkali metal salts such as sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tris-(2-hydroxyethyl)amine, cycloalkylamines such as dicyclohexylamine, or with procaine, dibenzylamine, N,N-dibenzylethylenediamine, 1-ephenamine, N-ethylpiperidine, N-benzyl-β-phenethylamine, dehydroabietylamine, N,N'-bisdehydroabietylamine, ethylenediamine, or bases of the pyridine type such as pyridine, collidine or quinoline, or other amines which have been used to form salts with known penicillins and cephalosporins.

Some of the compounds of this invention may be crystallised or recrystallised from solvents such as methanol. In such cases solvates may be formed. This invention includes within its scope stoichiometric solvates including hydrates as well as compounds containing variable amounts of water that may be produced by processes such as lyophilisation.

Since the compounds of the formula (I) and their salts and in-vivo hydrolysable esters are intended for use in pharmaceutical compositions it will readily be understood that they are each provided in substantially pure form, for example at least 60% pure, more suitably at least 75% pure and preferably at least 85%, especially at least 95% pure (% are on a weight for weight basis). Impure preparations of the compounds of the formula (I) and their salts may be used for preparing the more pure forms used in the pharmaceutical compositions; these less pure preparations of the compounds of formula (I) and their salts should contain at least 1%, more suitably at least 5% and preferably from 10 to 49% of a compound of the formula (I) or salt thereof.

Compounds of the present invention may exist as either syn or anti isomers, or may exist as mixtures of syn and anti isomers containing at least 75% of one such isomer, or preferably at least 90% of one such isomer.

Herein the terms syn and anti refer to the configuration of the group OR with respect to the carboxamido group, the syn-configuration (sometimes called the Z-configuration) being denoted thus:

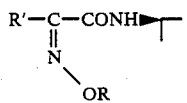

and the anti configuration (sometimes called the E-configuration) being denoted thus:

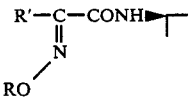

Preferred compounds of the present invention are the syn-isomers of the formula (II):

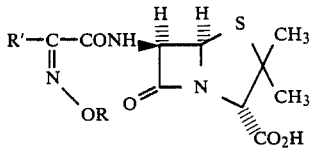

wherein R and $R^1$ are as hereinbefore defined.

Particularly preferred compounds within the present invention are 6β-[2-aminopyrid-6-yl)-(Z)-2-cyclohexyloxyiminoacetamido]penicillanic acid, 6β-[2-(4-aminopyrimid-2-yl)-2-(Z)-cyclohexyloxyiminoacetamido]penicillanic acid, 6β-[2-(5 amino-1,2,4-thiadiazol-3-yl)-2-(Z)-cyclohexyloxyiminoacetamido]penicillanic acid, 6-β-[2-(5-amino,1,2,4-thiadiazol-3-yl)2 (Z)tert-butyloxyiminonoacetamido] penicillanic acid or 6-β-[2-(5-amino, 1,2,4 thiadiazol-3-yl)2 (Z)cyclopentyloxyiminoacetamido penicillanic acid, or a pharmaceutically acceptable salts or in vivo hydrolysable esters thereof.

The compounds of formula (I) may be prepared by treating a compound of formula (III) or salt thereof:

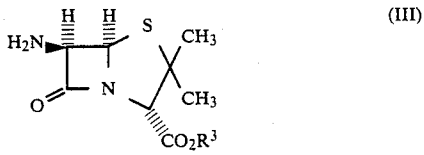

wherein the amino group is optionally substituted with a group which permits acylation to take place, and $R^3$ is hydrogen or a readily removable carboxyl blocking group; with an acylating agent derived from the acid of formula (IV):

wherein R and $R^1$ are as defined with respect to formula (I).

Any of the following reactions in any appropriate sequence may then be carried out:
 (i) removal of any amino-protecting group;
 (ii) removal of any carboxyl blocking group $R^3$;
 (iii) formation of a pharmaceutically acceptable salt;
 (iv) conversion of a carboxyl group into an ester function such as an in vivo hydrolysable ester.

Suitable groups which permit acylation to take place and which are optionally present on the amino group of the starting material of formula (III) include N-silyl, N-stannyl and N-phosphorus groups, for example trialkylsilyl groups such as trimethylsilyl, trialkyltin groups such as tri-n-butyltin, groups of formula $-PR^aR^b$ wherein $R^a$ is an alkyl, haloalkyl, aryl, aralkyl, alkoxy, haloalkoxy, aryloxy, aralkoxy or dialkylamino group, $R^b$ is the same as $R^a$ or is halogen or $R^a$ and $R^b$ together form a ring; suitable such phosphorus groups being $-P(OC_2H_5)_2$, $-P(C_2H_5)_2$,

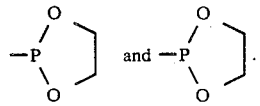

Suitable carboxyl-blocking derivatives for the group $CO_2R^3$ in formula (III) include salts and ester derivatives of the carboxylic acid. The derivative is preferably one which may readily be cleaved at a later stage of the reaction. Suitable salts include metal salts, such as those with sodium, potassium and lithium, and tertiary amine salts, such as those with trilower-alkylamines, N-ethylpiperidine, 2,6-lutidine, pyridine, N-methylpyrrolidine, dimethylpiperazine. A preferred salt is with triethylamine.

Suitable ester-forming carboxyl-blocking groups are those which may be removed under conventional conditions. Such groups for $R^3$ include benzyl, p-methoxybenzyl, 2,4,6-trimethylbenzyl, 3,5-di-t-butyl-4-hydroxybenzyl, benzoylmethyl, p-nitrobenzyl, 4-pyridylmethyl, 2,2,2-trichloroethyl, 2,2,2-tribromoethyl, t-butyl, t-amyl, diphenylmethyl (benzhydryl), triphenylmethyl, adamantyl,2-benzyloxyphenyl, 4-methylthiophenyl, tetrahydrofuran-2-yl, tetrahydropyran-2-yl, pentachlorophenyl, p-toluenesulphonylethyl, methoxymethyl, a silyl, stannyl or phosphorus-containing group, such as described above, an oxime radical of formula $-N=CHR^4$ where $R^4$ is aryl or heterocyclic, or an in vivo hydrolysable ester radical such as defined above.

The carboxyl group may be regenerated from any of the above esters by usual methods appropriate to the particular $R^3$ group, for example, acid—and base—catalysed hydrolysis, or by enzymically—catalysed hydrolysis, or by hydrogenation under conditions wherein other parts of the molecule are unaffected.

A reactive N-acylating derivative of the acid of formula (IV) is employed in the above process. The choice of reactive derivative will be influenced by the chemical nature of the group R, and of course the amino protecting group in the acid of formula (IV), when present, will be chosen such that the protected amino group does not react when the carboxy group in (IV) is converted into the said N-acylating derivative. Thus, in many—although not all—of the suitable N-acylating derivatives of the acid (IV) detailed below, the amino group must be protected.

A preferred amino-protecting group in the intermediate of formula (IV) is trityl, which group may suitably be removed from the product of formula (I) by treatment with formic acid.

Suitable N-acylating derivatives of the acid (V) include acid (IV) halides, preferably the acid chloride or bromide. Acylation with an acid halide may be effected in the presence of an acid binding agent, for example a tertiary amine (such as triethylamine or dimethylaniline), an inorganic base (such as calcium carbonate or sodium bicarbonate), molecular sieves (such as type 4 Angstroms) or an oxirane, which binds hydrogen halide liberated in the acylation reaction. The oxirane is preferably a $(C_{1-6})$- 1,2-alkylene oxide —such as ethylene oxide or propylene oxide. The acylation reaction using an acid halide may be carried out at a temperature in the range $-50°$ C. to $+50°$ C., preferably $-20°$ C. to $+20°$ C., in aqueous or non-aqueous media such as aqueous acetone, aqueous tetrahydrofuran, ethyl acetate, dimethylcetamide, dimethylformamide (DMF), acetonitrile, dichloromethane, 1,2-dichloroethane, or mixtures thereof. Alternatively, the reaction may be carried out in an unstable emulsion of water-immiscible solvent, especially an alihatic ester or ketone, such as methyl isobutyl ketone or butyl acetate.

The acid halide may be prepared by reacting the acid (IV) with a halogenating (e.g. chlorinating or brominating) agent such as phosphorus pentachloride, thionyl chloride or oxalyl chloride.

Alternatively, the N-acylating derivative of the acid (IV) may be a symmetrical or mixed anhydride. Suitable mixed anhydrides are alkoxyformic anhydrides, or anhydrides with, for example, carbonic acid monoesters, trimethyl acetic acid, thioacetic acid, diphenylacetic acid, benzoic acid, phosphorus acids (such as phosphoric or phosphorous acids) or aliphatic or aromatic sulphonic acids (such as methanesulphonic acid and p-toluenesulphonic acid respectively). When a symmetrical anhydride is employed, the acylation reaction may be carried out in the presence of an organic base such as 2,6-lutidine as catalyst.

When a mixed anhydride is employed the N-acylating derivative is preferably prepared in the presence of an organic base such as triethylamine and/or N,N-diisopropylethylamine in a suitable solvent such as DMF at between $-50°$ C. and room temperature. Alternatively, the N-acylating derivative may be prepared from an alkali metal salt of the acid of formula (IV), such as the sodium salt, in a suitable solvent such as DMF at between $-50°$ C. and room temperature. The N-acylating derivative of the acid of formula (IV) so derived may then be reacted with a compound of formula (III). The acylation reaction may conveniently be carried out at $-50°$ C. to $+50°$ C. in a suitable solvent such as water, acetonitrile or DMF at a temperature of not more than 0° C. The reaction may be carried out in the presence of a suitable base such as triethylamine or sodium hydrogen carbonate.

A further method of forming the N-acylating derivative of the acid of formula (IV) is to treat the acid of formula (IV) with a solution or suspension preformed by addition of a carbonyl halide, preferably oxalyl chloride, or a phosphoryl halide such as phosphorus oxychloride, to a halogenated hydrocarbon solvent, preferably dichloromethane, containing a lower acyl tertiary amide, preferably N,N-dimethylformamide. The N-acylating derivative of the acid of formula (IV) so derived may then be caused to react with a compound of formula (III). The acylation reaction may conveniently be carried out at $-40°$ to $+30°$ C., if desired in the presence of an acid binding agent such as triethylamine. A catalyst such as 4-dimethylaminopyridine may optionally also be added.

Other suitable acylating agents derived from the acid of formula (IV) are thioesters of formula (V)

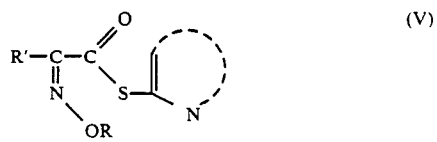

(V)

wherein R and $R^1$ are as hereinbefore defined and represents a 5- or 6-membered heterocyclic ring, which may contain, in addition to the nitrogen atom, one or two further heteroatoms, selected from oxygen, nitrogen and sulphur and which may be substituted or fused to a benzene ring which may itself be substituted.

Preferred acylating agents deried from the acid of formula (IV) are the thio esters (Va) or (Vb)

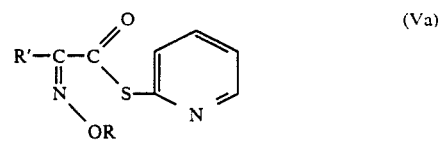

(Va)

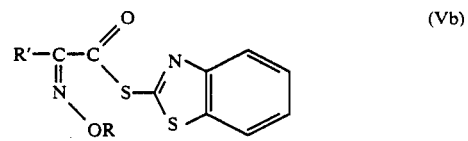

(Vb)

wherein R and $R^1$ are as hereinbefore defined.

Compounds of the formula (Va) and (Vb) may be prepared by treatment of the acid (IV) with 2,2'-dipyridyldisulphide or 2,2'-dibenzothiazolyldisulphide respectively, in the presence of triphenylphosphine, analogously to the routes described in EP-A-0037380. Conveniently, in compounds of the formula (Va) and (Vb), the amino group may be unprotected.

Other suitable N-acylating derivatives of acid (IV) include the acid azide; the activated esters derived from cyanomethanol; p-nitrophenol; 2,4-dinitrophenol; thiophenol; halophenols, including pentachlorophenol; monomethoxyphenol; N-hydroxy succinimide; N-hydroxybenzotriazole or 8-hydroxyquinoline; or include amides such as N-acylsaccharins, N-acylthiazolidin-2-thione or N-acylphthalimides; or an alkylidene iminoester prepared by reaction of the acid (IV) with an oxime.

When R is hydrogen, the hydroxyl group may advantageously be protected during the preparation of the N-acylating derivative of the acid of formula (IV) and/or during the coupling thereof with the compound of formula (III). Suitable protecting groups include trimethylsilyl and, more preferably, dimethyl-t-butylsilyl.

Compounds of formula (IV) may be prepared by routes analogous to those disclosed in GB-A-1,399,087, GB-A-2 025 398, and by Goto et al, J.Antibiotics [1984] 37(5), 532.

The present invention also provides a pharmaceutical composition which comprises a compound of formula (I) or a pharmaceutically acceptable salt or in vivo hydrolysable ester thereof and a pharmaceutically acceptable carrier. The compositions of the invention include those in a form adapted for oral, topical or parenteral use and may be used for the treatment of the infection in mammals including humans.

The antibiotic compounds according to the invention may be formulated for administration in any convenient way for use in human or veterinary medicine, by analogy with other antibiotics, and the invention therefore includes within its scope a pharmaceutical composition comprising a compound of formula (I) above together with a pharmaceutical carrier or excipient.

The composition may be formulated for administration by any route, such as oral, topical or parenteral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrollidone: fillers, for example lactose, sugar, maize-starch, calcium phosphate, sorbitol or glycine, tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminum stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampoule and sealing. Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration.

Where the composition comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I) is administered in the above-mentioned dosage range.

Compounds of the present invention are characterised by stability to $\beta$-lactamase producing organisms.

The compound of the invention of formula (I) may therefore be used as the sole therapeutic agent in compositions of the invention or may be used in combination with other antibiotics or with a $\beta$-lactamase inhibitor.

Advantageously the compositions also comprise a compound of formula (VI) or a pharmaceutically acceptable salt or ester thereof:

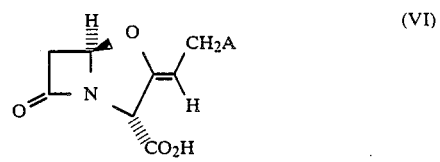
(VI)

wherein A is hydroxyl; substituted hydroxyl; thiol; a group of formula $SO_2R^5$ wherein $R^5$ is $C_{1-6}$ alkyl; substituted thiol; amino; mono- or di-hydrocarbyl substituted amino; mono- or di-acylamino; an optionally substituted triazolyl group; or an optionally substituted tetrazolyl group as described in EP 0 053 893.

A further advantageous composition comprises an antibiotic compound according to the invention and a pharmaceutically acceptable carrier or excipient together with a $\beta$-lactamase inhibitor of formula (VII) or a pharmaceutically acceptable salt or in vivo hydrolysable ester thereof:

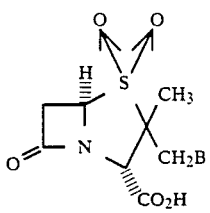

wherein B is hydrogen, halogen or a group of formula:

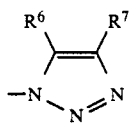

in which $R^6$ and $R^7$ are the same or different and each is hydrogen, $C_{1-6}$ alkoxycarbonyl, or carboxy or a pharmaceutically acceptable salt thereof.

Further suitable β-lactamase inhibitors include 6-alkylidene penem of formula VIII below:

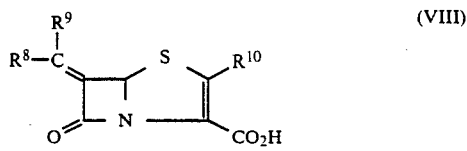

or a pharmaceutically acceptable salt or in vivo hydrolysable ester thereof, wherein $R^8$ and $R^9$ are the same or different and each represents hydrogen, or a $C_{1-10}$ hydrocarbon or heterocyclic group optionally substituted with a functional group; and $R^{10}$ represents hydrogen or a group of formula $R^a$ or $-SR^a$ where $R^a$ is an optionally substituted $C_{1-10}$ hydrocarbon or heterocyclic group, as described in European Patent Application No. 81301683.9 (Publication Number 0 041 768).

Other suitable β-lactamase inhibitors include 6β-bromopenicillanic acid and salts and in vivo hydrolysable esters thereof and 6β-iodopenicillanic acid and salts and in vivo hydrolysable esters thereof.

Such compositions of this invention comprising a β-lactamase inhibitor are formulated in conventional manner.

The present invention also includes a method of treating bacterial infections in humans and animals which comprises the administration of a therapeutically effective amount of an antibiotic compound of this invention.

Antibiotic compounds of the present invention are active against a broad range of bacteria, in particular they are useful for treatment of respiratory tract and urinary tract infections in humans and mastitis in cattle.

The antibiotic compounds of the present invention are active against both Gram-negative and Gram-positive organisms including *E.coli*, in particular ESS; *H.influenzae*, in particular Q1 and NEMC 1; *S.aureus* such as Oxford, Russell and MB 9; *S.pyogenes* such as CN10; *S. agalactiae* such as 2798 and *S.pneumoniae* such as PU7 and 1761.

The following Examples illustrates the present invention.

EXAMPLE 1 a. Ethyl 2-(2-triphenylmethylaminopyridin-6-yl) acetate.

A stirred solution of triphenylmethyl chloride (12.9 g) in methylene chloride (130 ml) was cooled in an ice bath and triethylamine (6.5 ml) was added. The mixture was stirred at 0° C. for 5 minutes and then a solution of ethyl 2-(2-aminopyridin-6-yl)acetate (8.35 g) in methylene chloride (35 ml) was added dropwise. The mixture was allowed to warm to room temperature for 1½ h, and then the solution was washed successively with two portions of water and then brine. The solution was dried over anhydrous magnesium sulphate and evaporated to give 21.2 gm of crude product which was used without further purification. $\nu_{max}$ (CHCl$_3$) 3420, 1725 cm$^{-1}$, δ(CDCl$_3$) 1.23 (3H, t, J=7Hz), 3.53 (2H, s), 4.12 (2H, q, J=7Hz), 5.66 (1H, d, J=8Hz), 6.07 (1H, s), 6.40 (1H, d, J =7Hz), 6.6–7.50 (16H, m).

b. Ethyl 2-(2-triphenylmethylaminopyridin-6-yl) glyoxylate.

A stirred solution of ethyl 2-(2-triphenylmethylaminopyridin-6-yl) acetate (4.22 g) in dioxan (20 ml) was heated to 85° to 90° C. and selenium dioxide (1.33 g) was added in portions over 30 minutes. The mixture was heated at 85° to 90° C. for 1h, then cooled, filtered and evaporated. The residue was dissolved in ethyl acetate, and the solution was washed with water, then brine, dried over anhydrous magnesium sulphate and evaporated. Column chromatography of the residue using gradient elution (Kieselgel, 10% increasing to 25% ethyl acetate in hexane) gave 2.54 g of product as a gum. $\nu_{max}$ (CHCl$_3$) 3420, 1740, 1700 cm$^{-1}$, δ(CDCl$_3$) 1.33 (3H, t, J=7Hz), 4.28 (2H, q, J=7 Hz), 6.0–6.3 (2H, m), 7.0–7.4 (17 H, m).

c. Ethyl 2-(2-triphenylmethylaminopyridin-6-yl) 2-hydroxy-iminoacetate.

A solution of hydroxylamine hydrochloride (2.10 g) in ethanol (50 ml) at 50° was added to a stirred solution of potassium hydroxide (1.69 g) in ethanol (25 ml). The solid was filtered off, and the filtrate added to a stirred solution of ethyl 2-(2-triphenylmethylaminopyridin-6-yl)acetate (13.18 g) in ethanol (20 ml). The mixture was heated to reflux for 15 minutes, cooled, and the solvent evaporated. The residue was partitioned between ethyl acetate and water, the organic phase was separated and washed with water, then brine, dried over anhydrous magnesium sulphate and evaporated. Column chromatography of the residue using gradient elution (Kieselgel, 1:5 going to 1:3 ethyl acetate : hexane) gave 7.23 g of product, $\nu_{max}$ (CHCl$_3$) 3410, 1725, 1590 cm$^{-1}$, δ(CDCl$_3$) 1.31 (3H, t, J=7Hz), 4.29 (2H, q, J=7Hz), 5.78 (1H, d, J=7Hz), 6.22 (1H, s), 6.7–7.3 (17H, m).

d. Ethyl 2(2-triphenylmethylaminopyridin-6-yl)-2-cyclohexyloxyiminoacetate.

Potassium carbonate (3.33 g) was added to a stirred solution of ethyl 2-(2-triphenylmethylaminopyridin-6-yl)2-hydroxyiminoacetate (7.23 g) in dimethyl sulphoxide (25 ml). Cyclohexyl iodide (3.70 g) was then added and the mixture stirred at room temperature for 3 days. The mixture was partitioned between ethyl acetate and water, and the organic phase was washed with three portions of water, then with brine, dried over anhydrous magnesium sulphate and evaporated. The product and unreacted starting material were isolated by column chromatography using gradient elution (Kieselgel, 10% going to 50% ethyl acetate in hexane). The procedure was repeated on the recovered starting material twice more. The samples of product were combined to give 4.47 g of a gum. $\nu_{max}$ (CHCl$_3$) 3420, 1730cm$^{-1}$. $\delta$(CDCl$_3$) 1.33 (3H, t, J=7Hz), 1.0-2.1 (10H, m), 3.9-4.5 (1H, m), 4.31 (2H, q, J=7Hz), 3.6-3.9 (1H, m), 6.00 (1H, s), 6.7-7.35 (17H, m).

e. Ethyl 2(2-aminopyridin-6-yl)2-cyclohexyloxyiminoacetate.

Water (15 ml) was added to a stirred solution of ethyl 2-(2-triphenylmethylaminopyridin-6-yl)2-cyclohexyloxyiminoacetate (4.47 g) in 98% formic acid (50 ml). The mixture was stirred for 3h and then the solvent was removed under reduced pressure. The residue was partitioned between ethyl acetate and water, the organic phase was separated and washed three times with water, then with brine, dried over anhydrous magnesium sulphate and evaporated. The product was purified by column chromatography using gradient elution (Kieselgel 50% ethyl acetate in hexane going to 100% ethyl acetate) to give 2.11 g of product as a gum. $\nu_{max}$ (film) 3480, 3380, 1735, 1620 cm$^{-1}$, $\delta$(CDCl$_3$) 1.0-2.1 (10H, m), 1.35 (3H, t, J=7 Hz), 3.9-4.9 (3H, m), 4.36 (2 H, q, J=7 Hz), 6.36 (1H, dd, J=1 and 7 Hz), 7.0-7.5 (2H, m).

f. 2(2-Aminopyridin-6-yl) 2-cyclohexyloxyiminoacetic acid.

Sodium hydroxide solution (14.5 ml of 1N) was added to a stirred solution of ethyl 2(2-aminopyridin-6-yl)2-cyclohexyloxyiminoacetate (2.11 g) in ethanol. The mixture was stirred at room temperature overnight and then the ethanol was removed under reduced pressure. The aqueous solution was washed with ethyl acetate and then air was passed through the solution to remove residual ethyl acetate. Dilute hydrochloric acid (29 ml of 0.5 N) was then added. The solid was filtered off, washed with water and dried under vacuum to give 1.48 g of product, m.p. 218-219° C. $\nu_{max}$ (nujol) 3380, 3160, 1665, 1630cm$^{-1}$.

g. Sodium 6-$\beta$-[2-(2-aminopyridin-6-yl) 2-(Z)-cyclohexyl-oxyiminoacetamido]penicillinate.

A stirred suspension of 2-(2-aminopyridin-6-yl)-2-cyclohexyloxyiminoacetic acid (526 mg) and N,N-diisopropylethylamine (0.382 ml) in dimethylformamide (2 ml) was cooled to −50° C. to −60° C. and methanesulphonyl chloride (0.17 ml) was added. The mixture was stirred at this temperature for 40 minutes and then added to a stirred solution of triethylammonium 6-aminopenicillinate (634 mg) in water (1 ml) at 0°. The mixture was stirred overnight and the product was separated by column chromatography using gradient elution (Kieselgel 7:2:1 going to 5:4:2 ethyl acetate : isopropanol : water as eluent). Fractions containing product were combined, sodium bicarbonate solution (2 ml of saturated solution) was added and the mixture evaporated. The product was purified by column chromatography on HP20SS with water containing increasing proportions of acetone as eluent. Fractions containing product were combined and evaporated to about 30 ml and freeze-dried to give 470 mg of product. $\nu_{max}$ (KBr) 1769, 1670, 1612 cm$^{-1}$, $\delta$[(CD$_3$)$_2$SO]1.0-2.1 (10 H, m), 1.47 (3 H, s) 1.55 (3 H, s), 3.88 (1 H, s) 3.9-4.3 (1 H, m), 5.35-5.65 (2 H, m), 5.89 (2 H, broad s), 6.54 (1 H, d, J=8 Hz), 6.84 (1 H, d, J=8 Hz), 7.37 (1 H, t, J=8 Hz), 8.93 (1 H, d, J=9 Hz).

In Vitro Biological Data.

The compound of the Example was tested in vitro against a number of microorganisms. The results of these tests are shown in the following table:

| | MIC ($\mu$g/ml) |
|---|---|
| H. influenzae Q1 | 1.0 |
| H. influenzae NEMC1 | 1.0 |
| E. Coli ESS | 0.12 |
| B. catarrhalis Ravasio | 0.5 |
| S. aureus Oxford | 0.5 |
| S. aureus Russell | 0.5 |
| S. aureus MB9 | 2.0 |
| S. epidermidis PHLN20 | 0.5 |
| S. pyogenes CN10 | <0.03 |
| S. agalacticae 2798 | 0.25 |
| S. pneumoniae 1761 | <0.03 |

EXAMPLE 2 a. Dimethyl cyclohexyloxyiminomalonate.

Potassium carbonate (25 g) was added to a stirred solution of dimethyl hydroxyiminomalonate (17.4 g) in dimethyl sulphoxide (40 ml). Cyclohexyl bromide (17.4 g) was then added and the mixture was stirred for 4 days at room temperature. The mixture was partitioned between ethyl acetate and water, and the organic phase was washed four times with water, then with brine, dried over magnesium sulphate and evaporated. Chromatography of the residue (Kieselgel, 10% ethyl acetate in hexane) gave 13.8 g of product, $\nu$max (film) 1750 cm$^{-1}$, $\delta$(CDCl$_3$) 1.1-2.3 (10 H, m), 3.94 (6 H, s), 4.1-4.7 (1 H, m).

b. Methyl 2-carbamoyl-2-cyclohexyloxyiminoacetate.

Concentrated aqueous ammonia solution (7.2 ml) was added to a stirred solution of dimethyl cyclohexyloxyiminomalonate (10.11 g) in methanol (20 ml). The mixture was stirred at room temperature for 2 ½ hr. and then most of the solvent was removed under vacuum. The residue was partitioned between ethyl acetate and water. The organic phase was separated, washed with water, then brine, dried over anhydrous magnesium sulphate and evaporated. The residue was recrystallised from ethyl acetate/60°-80° petroleum ether to give 7.77 g of product, m.p. 92°-99° (Found: C, 52.60; H, 7.08; N, 12.62; C$_{10}$H$_{16}$N$_2$O$_4$ requires: C, 52.62; H, 7.07; N, 12.27), $\nu_{max}$(nujol) 3420, 3160, 1740, and 1680 cm$^{-1}$, $\delta$(CDCl$_3$) 1.0-2.2 (10 H, m), 3.92 (3 H, s), 4.0-4.6 (1 H, m), 6.51 (2H, broad s).

c. Methyl 2-cyano-2-cyclohexyloxyiminoacetate.

A solution of methyl 2-carbamoyl-2-cyclohexyloxyiminoacetate (6.84 g) in pyridine (50 ml) was cooled in an ice bath and trifluoroacetic anhydride (15.7 g) was added at such a rate that the temperature remained below 25°. When the addition was complete the mixture was stirred at room temperature for 30 minutes and then poured into a mixture of 200 ml of water and 100 ml of ethyl acetate. The mixture was adjusted to pH2 by the addition of 5N hydrochloric acid. The organic phase was separated and washed successively with 5N hydrochloric acid, water, sodium bicarbonate solution, water and brine. The solution was dried over anhydrous magnesium sulphate and evaporated to give 6.23 g of product, $\nu_{max}$ (film) 2240, and 1750 cm$^{-1}$, $\delta$(CDCl$_3$) 1.1-2.2 (10 H, m), 3.93 (3H, s), 4.1-4.7 (1 H, m).

d. Methyl 3-imino-3-methoxy-2-cyclohexyloxyiminoacetate.

Sodium methoxide solution (5 ml of 1N in methanol) was added to a stirred solution of methyl 2-cyano-2-cyclohexyloxyiminoacetate (6.23 g) in methanol (50 ml) cooled in an ice bath. The mixture was stirred at 0° for 1½ hr, and then acetic acid (0.3 ml) was added and the solvent evaporated. The residue was partitioned between water and dichloromethane, and the organic phase was washed with water, then brine, dried over MgSO$_4$ and evaporated. Chromatography of the residue using gradient elution (Kieselgel 9:1 going to 3:1 hexane:ethyl acetate) gave 6.05 g of product, $\nu_{max}$(film) 3320, 1740, and 1655 cm$^{-1}$, δ(CDCl$_3$) 1.1–2.2 (10 H, m), 3.57 (6 H, s), 4.1–4.6 (1 H, m), 8.3 (1 H, broad s).

e. Methyl 2-amidino-2-cyclohexyloxyiminoacetate hydrochloride.

Ammonium chloride (1.55 g) was added to a stirred solution of methyl 3-imino-3-methoxy-2-cyclohexyloxyiminoacetate (6.68 g) in methanol (30 ml). The mixture was heated at reflux for 2 hr, cooled and the solvent evaporated under reduced pressure. The residue was triturated with ether and the solid filtered off, washed with ether and dried under vacuum to give 5.18 g of solid m.p. 181°–183° $\nu_{max}$ (nujol) 1745, 1680, and 1605 cm$^{-1}$. The product was used without further purification.

f. Methyl 2(4-aminopyrimid-2-yl) 2-cyclohexyloxyiminoacetate.

A stirred suspension of methyl 2-amidino-2-cyclohexyloxyiminoacetate hydrochloride (2.64 g) in methanol (10 ml) was cooled in an ice bath and 2-chloroacrylonitrile (0.8 ml) was added followed by triethylamine (2.8 ml) added dropwise. The stirred mixture was allowed to warm to room temperature overnight. The solvent was then evaporated and the residue partitioned between ethyl acetate and water. The organic phase was separated and washed with water, then brine, dried over anhydrous magnesium sulphate and evaporated. Column chromatography of the residue using gradient elution (Kieselgel 3:1 hexane:ethyl acetate going to ethyl acetate) gave 1.51 g of product m.p. 138.5–140.5° from ethyl acetate/60°–80° petroleum ether (Found: C 56.04; H, 6.28; N, 19.81: C$_{13}$H$_{18}$N$_4$O$_3$ requires: C, 56.10; H, 6.52; N, 20.13), $\nu_{max}$ (nujol) 3460, 3310, 3170, 1735, and 1640 cm$^{-1}$, δ(CDCl$_3$) 1.0–2.1 (10 H, m), 3.96 (3 H, s), 4.1–4.6 (1 H, m), 5.66 (2 H, broad s), 6.43 (1 H, d, J=6Hz), 8.25 (1 H, d, J=6Hz).

g. 2-(4-Aminopyrimid-2-yl) 2-cyclohexyloxyiminoacetic acid.

Sodium hydroxide solution (10.85 ml of 1N) was added to a stirred solution of methyl 2-(4-amino-pyrimid-2-yl) -2-cyclohexyloxyiminoacetate in ethanol (20 ml). The mixture was stirred overnight and then the ethanol was evaporated under reduced pressure. Dilute hydrochloric acid (21.7 ml of 0.5 N) was added to the residue and the solution evaporated to dryness, and the residue dried under vacuum. The residue was extracted with a boiling 1:1 mixture of ethyl acetate:ethanol, after filtering and cooling the extract the solid which crystallised was filtered off, washed with ethyl acetate and dried under vacuum to give 1.04 g of product m.p. 132°–134°, $\nu_{max}$ (nujol) 1630 cm$^{-1}$, δ[(CD$_3$)$_2$SO]0.9–2.1 (10 H, m), 3.9–4.4 (1 H, m), 6.46 (1 H, d, J=6 Hz), 7.13 (2 H, br s), 8.16 (1 H, d, J=6 Hz).

h. Sodium 6-β-[2-(4-aminopyrimid-2-yl)-2-(Z)cyclohexyloxyiminoacetamido]penicillinate.

N,N-Diisopropylethylamine (0.382 ml) was added to a stirred solution of 2-(4-aminopyrimid-2-yl)-2-cyclohexyloxyiminoacetic acid (528 mg) in dimethylformamide (2 ml). The mixture was cooled to −50° to −60°. Methanesulphonyl chloride (0.17 ml) was added and the mixture was then allowed to warm up until all the solid dissolved, the mixture was then cooled to −50° to −60° C. for 40 minutes. The mixture was then added to a stirred solution of triethylammonium 6-aminopenicillinate (634 mg) in water (1 ml) at 0°. The mixture was stirred fr 4 hr and the product separated by column chromatography of the mixture using gradient elution (Kieselgel 7:2:1 going to 5:4:2 ethyl acetate:isopropanol:water as eluent. Fractions containing product were combined, sodium bicarbonate solution (2 ml of saturated solution) was added and the mixture evaporated. The product was purified by column chromatography on HP20SS with water containing increasing proportions of acetone as eluent. Fractions containing product were combined and evaporated to about 30 ml and then freeze dried to give 430 mg of product, $\nu_{max}$ (KBr) 1768, 1603 cm$^{-1}$, δ[(CD$_3$)$_2$SO] 1.0–2.1 (10H, m), 1.47 (3H, s), 1.55 (3H, s), 3.88 (1H, s), 3.95–4.3 (1H, m), 5.35–5.65 (2H, m), 6.39 (1H, d, J=7 Hz), 7.00 (2H, broad s), 8.02 (1H, d, J=7 Hz), 8.88 (1H, d, J=8 Hz).

EXAMPLE 3

Steps a–e of previous example were followed by:

f. Methyl 2-(5-amino 1,2,4 thiadiazol-3-yl)2-cyclohexyloxyiminoacetate.

Triethylamine (2.52 g) was added to a stirred solution of methyl 2-amidino-2-cyclohexyloxyiminoacetate hydrochloride (2.64 g) in methanol (30 ml) cooled to −5° to −10° C. Bromine (1.65 g) was then added dropwise. A solution of potassium thiocyanate (0.97 g) in methanol (10 ml) was then added maintaining the temperature at −5° to −10° C. When the addition was complete the mixture was allowed to warm to 0° to 5° for 2 hr. The solvent was removed under reduced pressure and the residue partitioned between ethyl acetate and water. The organic phase was separated, washed with water, then brine, dried over anhydrous magnesium sulphate and evaporated. The residue was recrystallised from ethyl acetate/60°–80° petroleum ether to give 1.81 g of product m.p. 177°–179° $\nu_{max}$ (nujol) 3440, 3260, 3120, 1725, and 1615 cm$^{-1}$, δ(CDCl$_3$) 1.1–2.1 (10 H, m), 3.96 (3H, s), 4.1–4.5 (1 H, m), 6.70 (2H, broad s).

g. 2-(5-Amino 1,2,4 thiadiazol-3-yl)2-cyclohexyloxyiminoacetic acid.

Sodium hydroxide solution (12.76 ml of 1N) was added to a stirred suspension of methyl 2-(5-amino 1,2,4 thiadiazol-3-yl)2-cyclohexyloxyiminoacetate (1.81 g) in ethanol (20 ml). After 5 hr most of the ethanol was removed on a rotary evaporator, dilute hydrochloric acid (25.52 ml of 0.5N) was added to the residue and the mixture cooled in an ice bath. The solid was filtered off, washed with water and dried under vacuum. The solid was dissolved in acetone and triturated with 60°–80° petroleum ether, the solid was filtered off, washed with 60°–80° petroleum ether and dried under vacuum to give 1.38 g of product $\nu_{max}$ (nujol) 1710, 1615 cm$^{-1}$, δ[(CD$_3$)$_2$SO] 0.9–2.2 (10 H, m), 3.9–4.5 (1H, m), 8.2 (2H, broad s).

h. Sodium 6-β-[2-(5-amino 1,2,4 thiadiazol-3-yl) 2 (Z) cyclohexyloxyiminoacetamido]penicillinate.

N,N-Diisopropylethylamine (0.382 ml) was added to a stirred solution of 2-(5-amino 1,2,4 thiadiazol-3-yl) 2-cyclohexyloxyiminoacetic acid (540 mg) in dimethylformamide (2 ml). The mixture was cooled to −50° to −60° C. and methanesulphonyl chloride (0.17 ml) was added, the mixture was stirred at −50° to −60° C. for 40 minutes and then added to a stirred solution of triethylammonium 6-aminopenicillanate (634 mg) in water (1 ml) at 0°C. The mixture was stirred overnight and then the product was isolated by column chromatography of the mixture (Kieselgel, 7:2:1 ethyl acetate:isopropanol:water as eluent). Fractions containing product were combined, saturated sodium bicarbonate solution (2 ml) was added, and the solution evaporated. The product was purified by HP20SS chromatography using water with increasing proportions of acetone as eluent. Fractions containing product were evaporated to about 10 ml, diluted to 30 ml with water and freeze dried to give 238 mg of product $\nu_{max}$ (KBr) 1767, 1670 and 1609 cm$^{-1}$, $\delta[(CD_3)_2SO]$ 1.0–2.0 (10H, m), 1.47 (3H, s), 1.55 (3H, s), 3.89 (1H, s), 3.9–4.25 (1H, m), 5.35–5.60 (2H, m), 6.17 (2H, broad s), 9.09 (1H, d, J=8 Hz).

EXAMPLE 4 a. Dimethyl tert-butyloxyiminomalonate.

Zinc chloride (2.73 g) and 4A molecular sieves (6 g) were added to a stirred solution of dimethyl hydroxyiminomalonate (3.22 g) and tert-butanol (1.48 g) in dichloromethane (50 ml). The mixture was heated at reflux for 72 hr., then cooled and the solid filtered off. The filtrate was washed three times with water, then with brine, dried over anhydrous magnesium sulphate and evaporated. Column chromatography of the residue using gradient elution (Kieselgel, 5% going to 10% ethyl acetate in hexane) gave 1.06 g of product, $\nu_{max}$ (CHCl$_3$) 1743 cm$^{-1}$, $\delta$(CDCl$_3$) 1.38 (9H, s) 3.89 (6H, s).

The following compounds were prepared by the same methods as used in the analogous step in the cyclohexyl series.

b. Methyl 2-carbamoyl-2-tert-butyloxyiminoacetate.

Dimethyl tert-butyloxyiminomalonate (10.85 g) gave 7.18 g of product, m.p. 129.5°–131° (Found: C, 47.84; H, 7.17; N, 13.72; C$_8$H$_{14}$N$_2$O$_4$ requires: C, 47.52; H, 6.98; N, 13.85), $\nu_{max}$ (CHCl$_3$) 3520, 3402, 1745, 1692 cm$^{-1}$, $\delta$(CDCl$_3$) 1.37 (9H, s), 3.91 (3H, s), 6.05 (1 H, broad) 6.45 (1H, broad).

c. Methyl 2-cyano-2-tert-butyloxyiminoacetate

Methyl 2-carbamoyl-2-tert-butyloxyiminoacetate (7.18 g) gave 5.79 g of product $\nu_{max}$ (CHCl$_3$) 2240, 1750 cm$^{-1}$ $\delta$(CDCl$_3$) 1.42 (9H, s) 3.86 (3H, s).

d. Methyl 3-imino-3-methoxy-2-tert-butyloxyiminopropionate

Methyl 2-cyano-2-tert-butyloxyiminoacetate (5.79 g) gave 6.72 g of product, $\nu_{max}$ (CHCl$_3$) 3325, 1740, 1658 cm$^{-1}$ $\delta$(CDCl$_3$) 1.35 (9H, s), 3.89 (6H, s), 7.92–859 (1H, broad s).

e. Methyl 2-amidino-2-tert-butyloxyiminoacetate hydrochloride.

Methyl 3-imino-3-methoxy-2-tert-butyloxyiminopropionate (6.72 g) gave 4.65 g of product m.p. 196.5°–198° $\nu_{max}$(Nujol) 1745, 1680 cm$^{-1}$ $\delta[(CD_3)_2SO]$ 1.37 (9H, s), 3.88 (3H, s), 7.99–10.06 (4H, broad).

f. Methyl 2-(5-amino 1,2,4 thiadiazol-3-yl)2-tertbutyloxyiminoacetate.

Methyl 2-amidino-2-tert-butyloxyiminoacetate hydrochloride (4.41 g) gave 3.15 g of product m.p. 196°–197.5° (Found: C, 41.82; H, 5.47; N, 20.85; S, 12.66; C$_9$H$_{14}$N$_4$O$_3$S requires; C, 41.85; H, 5.46 N, 21.69; S, 12.41), $\nu_{max}$ (Nujol) 3410, 3260, 3125, 1743, 1624 cm$^1$ $\delta[(CD_3)_2SO]$ 1.34 (9H, s), 3.91 (3H, s), 8.40 (2H, broad s).

g. 2-(5-Amino 1,2,4 thiadiazol-3-yl)2-tertbutyloxyiminoacetic acid.

Methyl 2-(5-amino 1,2,4 thiadiazol-3-yl)2-tert-butyloxyiminoacetate (3.05 g) gave 0.72 g of product m.p. 190°–194°, $\nu_{max}$ (Nujol) 3300, 3180, 1708, 1622 cm$^{-1}$ $\delta[(CD_3)_2SO]$ 1.34 (9H, s), 8.37 (2H, s).

h. Sodium 6-$\beta$-[2-(5-amino 1,2,4 thiadiazol-3-yl)2 (Z)tert-butyloxyiminoacetamido]penicillinate.

2-(5-Amino 1,2,4 thiadiazol-3-yl)$_2$-tert-butyloxyiminoacetic acid (0.488 g) gave 0.235 g of product, $\nu_{max}$ (KBr) 1768, 1610 cm$^{-1}$ $\delta[(CD_3)_2SO]$ 1.28 (9H, s), 1.48 (3H, s), 1.57 (3H, s), 3.94 (1H, s), 5.43 (1H, d, J=3.9 Hz), 5.53 (1H, dd, J=3.8 and 8.3 Hz), 8.21 (2H, s), 9.20 (1H, d, J=8.4 Hz).

EXAMPLE 5 a. Dimethyl cyclopentyloxyiminoacetate

Dimethyl hydroxyiminomalonate (21.19 g) gave 20.58 g of product, $\nu_{max}$ (CHCl$_3$) 1742 cm$^{-1}$ $\delta$(CDCl$_3$) 1.35–2.15 (8H, m), 3.92 (6H, s) 4.75–5.19 (1H, m).

b. Methyl-2-carbamoyl-2-cyclopentyloxyiminoacetate.

Dimethyl cyclopentyloxyiminoacetate (20.58 g) gave 15.52 g of product m.p. 90.5°–93°, (Found; C, 50.57; H, 6.77; N, 12.93; C$_9$H$_{14}$N$_2$O$_4$ requires; C, 50.46; H, 6.59; N, 13.08), $\nu_{max}$ (CHCl$_3$) 3525, 3410, 1747 and 1695 cm$^{-1}$ $\delta$(CDCl$_3$) 1.31–2.20 (8H, m), 3.90 (3H, s), 4.62–5.05 (1H, m) 5.72–6.72 (2 H, broad).

c. Methyl 2-cyano-2-cyclopentyloxyiminoacetate.

Methyl-2-carbamoyl-2-cyclopentyloxyiminoacetate (13.36 g) gave 11.99 g of product, $\nu_{max}$ (CHCl$_3$) 2240, 1750 cm$^{-1}$ $\delta$(CDCl$_3$) 1.40–2.21 (8H, m), 3.92 (3H, s), 4.84–5.26 (1H, m).

d. Methyl 3-imino-3-methoxy-2-cyclopentyloxyiminopropionate.

Methyl 2-cyano-2-cyclopentyloxyiminoacetate (13.56 g) gave 12.84 g of product, $\nu_{max}$ (CHCl$_3$) 3315, 1743, 1657 cm$^{-1}$ $\delta$(CDCl$_3$), 1.37–2.20 (8H, m), 3.89 (6H, s), 4.70–5.10 (1H, m).

e. Methyl 2-amidino-2-cyclopentyloxyiminoacetate hydrochloride.

Methyl 3-imino-3-methoxy-2-cyclopentyloxyiminopropionate (10.84 g) gave 7.85 g of product, m.p. 170°–178° (Found; C, 43.34, H, 6.48; N, 16.87, Cl, 13.90; C$_9$H$_{16}$ClN$_3$O$_3$ requires; C, 43.41; H, 6.46; N, 16.83; Cl, 14 20), $\nu_{max}$ (Nujol) 1742, 1679 cm$^{-1}$ $\delta[(CD_3)_2SO]$ 1.34–2.15 (8H, m), 3.86 (3H, s), 4.7–5.22 (1H, m), 8.95–10.45 (4H, m).

f. Methyl 2-(5-amino 1,2,4 thiadiazol-3-yl)2-cyclopentyloxyiminoacetate.

Methyl 2-amidino-2-cyclopentyloxyiminoacetate hydrochloride (7.85 g) gave 5.58 g of product m.p. 189°–190.5° (Found; C, 44.68; H, 5.30; N, 20.54; C$_{10}$H$_{14}$N$_4$O$_3$S requires: C, 44.43; H, 5.22; N, 20.73). $\nu_{max}$ (Nujol) 3420, 3350, 3250, 1750, 1730, 1620 cm$^{-1}$ $\delta[(CD_3)_2SO]$ 1.33–2.16 (8H, m), 3.85 (3H, s), 4.63–5.02 (1H, m), 8.22 (2H, broad s).

g. 2-(5-Amino 1,2,4 thiadiazol-3-yl)-2-cyclopentyloxyiminoacetic acid.

Methyl 2-(5-amino 1,2,4 thiadiazol-3-yl)2-cyclopentyloxyiminoacetate (5.35 g) gave 1.16 g of product, $\nu_{max}$ (Nujol) 3420, 3260, 3175, 3149, 1722 and 1617 cm$^{-1}$ $\delta[(CD_3)_2SO]$ 1.35–2.08 (8H, m) 4.58–5.00 (1H, m), 7.79–8.53 (2H, broad s).

h. Sodium 6-$\beta$-[2-(5-amino 1,2,4 thiadiazol-3-yl) 2 (Z)cyclopentyloxyiminoacetamido]penicillinate.

2-(5-Amino 1,2,4 thiadiazol-3-yl)2-cyclopentyloxyiminoacetic acid (0.513 g) gave 0.338 g of product. $\nu_{max}$ (KBr) 1765, 1609 cm$^{-1}$ $\delta$(CD$_3$)$_2$SO] 1.45 (3H, s) 1.5–1.95 (8H, m), 1.55 (3H, s), 3.83 (1H, s), 4.62–4.79 (1H, m), 5.37 (1H, d, J=4 Hz), 5.46 (1H, dd, J=3.9 and 8.2 Hz), 8.172 (H, s), 9.23 (1H, d, J=8.3 Hz).

We claim:

1. A compound of formula (I) or a pharmaceutically acceptable salt or in-vivo hydrolysable ester thereof:

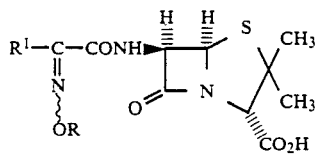
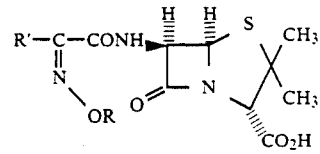

wherein $R^1$ is a 5 or 6 membered heterocycle containing 1 or 2 nitrogen atoms or 1 or 2 nitrogen atoms and 1 sulphur atom substituted by amino with the proviso, however, that $R^1$ is not 2-aminothiazol-4-yl; and R is hydrogen; alkenyl of 2 to 12 carbon atoms unsubstituted or substituted by carboxyl, esterified carboxyl, carbonyl, hydroxy, alkoxy, of 1 to 6 carbon atoms, cyano, carbamoyl, aryloxy, aralkoxy of 1 to 6 carbon atoms in the alkoxy moiety, mercapto, alkylthio of 1 to 6 carbon atoms, arylthio, amino, halo, nitro, azido, formyl, acyl, acyloxy, phthalimido, acylamino, alkoxycarbonylamino of 1 to 6 carbon atoms in the alkoxy moiety, aralkoxy-carbonylamino of 1 to 6 carbon atoms in the alkoxy moiety, heterocyclyl or carbocyclyl; alkynyl of 2 to 12 carbon atoms unsubstituted or substituted by carboxyl, esterified carboxyl, carbonyl, hydroxy, alkoxy of 1 to 6 carbon atoms, cyano, carbamoyl, aryloxy, aralkoxy of 1 to 6 carbon atoms in the alkoxy moiety, mercapto, aklylthio of 1 to 6 carbon atoms, arylthio, amino, halo, nitro, azido, formyl, acyl, acyloxy, phthalimido, acylamino, alkoxycarbonylamino of 1 to 6 carbon atoms in the alkoxy moiety, aralkoxy-carbonylamino of 1 to 6 carbon atoms in the alkoxy moiety, heterocyclyl or carbocyclyl; carbocyclyl of 1 to 4 rings unsubstituted or substituted by alkyl of 1 to 6 carbon atoms, alkenyl of 2 to 6 carbon atoms, alkynyl of 2 to 6 carbon atoms, exomethylene, carboxyl, alkoxycarbonyl of 1 to 6 carbon atoms in the alkoxy moiety, oxo, hydroxy, alkoxyimino of 1 to 6 carbon atoms, oxyimino, alkoxy of 1 to 6 carbon atoms, cyano, carbamoyl, aryloxy, aralkoxy of 1 to 6 carbon atoms in the alkoxy moiety, mercapto, alkylthio, arylthio, amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, heterocyclyl or carbocyclyl; or heterocyclyl unsubstituted or substituted by halo, alkyl of 1 to 6 carbon atoms, carbocyclyl, alkylthio, acylamino, alkoxy of 1 to 6 carbon atoms, haloalkyl of 1 to 6 carbon atoms, hydroxy, amino, carboxy, carbamoyl, acyl, alkoxycarbonyl of 1 to 6 carbon atoms, alkoxycarbonylalkyl of 1 to 6 carbon atoms in the alkoxy moiety and 1 to 6 carbon atoms in the alkyl moiety, aryl or oxo.

2. A compound according to claim 1, wherein $R^1$ is a member selected from the group consisting of aminopyridyl, amino-pyrimidyl and aminothiadiazole.

3. A compound according to claim 1, wherein R is partly saturated carbocyclyl.

4. A compound according to claim 1, wherein R is alkyl, alkenyl or alkynyl of 3 to 6 carbon atoms having a secondary or tertiary carbon atom at the point of attachment to the oxyimino moiety.

5. A compound according to claim 1, wherein R is cyclopentyl, cyclohexyl or t-butyl.

6. A compound according to claim 1, which is the syn-isomer of formula (II):

or a pharmaceutically acceptable salt or in vivo hydrolysable ester thereof.

7. A compound according to claim 6 or a pharmaceutically acceptable salt or in-vivo hydrolysable ester thereof wherein R is cyclohexyl.

8. A compound according to claim 1, which is a member selected from the group consisting of 6β-[2-aminopyridol-6-yl)-(Z)-2-cyclohexyloxyiminoacetamido]penicillanic acid, 6β-[2-(4-aminopyrimid-2-yl)-2-(Z)-cyclohexyloxyiminoacetamido]penicillanic acid, and 6β-[2-(5-amino 1,2,4 thiadiazol-3-yl)-2-(Z)-2-cyclohexyloxyiminoacetamido]penicillanic acid, 6-β-[2-(5-amino 1,2,4-thiadiazol-3-yl)2(Z)tertbutyloxyiminonoacetamido]penicillanic acid or 6-β-[2-(5-amino,1,2,4 thiadiazol-3-yl)2(Z)cyclopentyloxyiminoacetamido]penicillanic acid.

9. A compound of formula (IV) or a salt, ester, or acylating derivative thereof;

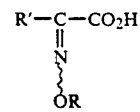

wherein $R^1$ is a 5 or 6 membered heterocycle containing 1 to 6 nitrogen atoms or 1 or 2 nitrogen atoms and 1 sulphur atom substituted by amino with the proviso, however, that $R^1$ is not 2-aminothiazol-4-yl; and R is hydrogen; alkyl of 1 to 12 carbon atoms unsubstituted or substituted by carboxyl, esterified carboxyl, carbonyl, hydroxy, alkoxy of 1 to 6 carbon atoms, cyano, carbamoyl, aryloxy, aralkoxy of 1 to 6 carbon atoms in the alkoxy moiety, mercapto, alkylthio of 1 to 6 carbon atoms, arylthio, amino, halo, nitro, azido, formyl, acyl, acyloxy, phthalimido, acylamino, alkoxycarbonylamino of 1 to 6 carbon atoms in the alkoxy moiety, aralkoxy-carbonylamino of 1 to 6 carbon atoms in the alkoxy moiety, heterocyclyl or carbocyclyl; alkenyl of 2 to 12 carbon atoms unsubstituted or substituted by carboxyl, esterified carboxyl, carbonyl, hydroxy, alkoxy of 1 to 6 carbon atoms, cyano, carbamoyl, aryloxy, aralkoxy of 1 to 6 carbon atoms in the alkoxy moiety, mercapto, alkylthio of 1 to 6 carbon atoms, arylthio, amino, halo, nitro, azido, formyl, acyl acyloxy, phthalimido, acylamino, alkoxycarbonylamino of 1 to 6 carbon atoms in the alkoxy moiety, aralkoxy-carbonylamino of 1 to 6 carbon atoms in the alkoxy moiety, heterocyclyl or carbocyclyl; alkynyl of 2 to 12 carbon atoms unsubstituted or substituted by carboxyl, esterified carboxyl, carbonyl, hydroxy, alkoxy of 1 to 6 carbon atoms, cyano, carbamoyl, aryloxy, aralkoxy of 1 to 6 carbon atoms in the alkoxy moiety, mercapto, alkylthio, arylthio, amino, halo, nitro, azido, formyl, acyl, acyloxy, phthalimido, acylamino, alkoxycarbonylamino of 1 to 6 carbon atoms in the alkoxy moiety, aralkoxy-carbonylamino of 1 to 6 carbon atoms in the alkoxy moiety, heterocyclyl or carbocyclyl; carbocyclyl of 1 to 4 rings unsubstituted or substituted by alkyl of 1 to 6 carbon atoms, alkenyl of 2 to 6 carbon atoms, alkynyl of 2 to 6 carbon atoms, exo-methylene, carboxyl, alkoxycarbonyl of 1 to 6 carbon atoms in the alkoxy moiety, oxo, hydroxy, alkoxyimino of 1 to 6 carbon atoms, oxyimino, alkoxy of 1 to 6 carbon atoms, cyano, carbamoyl, araloxy, aralkoxy of 1 to 6 carbon atoms in the alkoxy moiety, mercapto, alkylthio of 1 to 6 carbon atoms, arylthio, amino, halo, nitro, azido, formyl, acyl, acryloxy, phthalimido, acylamino, alkoxycarbonylamino of 1 to 6 carbon atoms in the alkoxy moiety, aralkoxycarbonylamino of 1 to 6 carbon atoms in the alkoxy moiety, heterocyclyl or carbocyclyl; or heterocyclyl unsubstituted or substituted by halo, alkyl of 1 to 6 carbon atoms, carbocyclyl, alkylthio, acylamino, alkoxy of 1 to 6 carbon atoms, haloalkyl of 1 to 6 carbon atoms, hydroxy, amino, carboxy, carbamoyl, acyl, alkoxycarbonyl of 1 to 6 carbon atoms, alkoxycarbonylalkyl of 1 to 6 carbon atoms in the alkoxy moiety and 1 to 6 carbon atoms in the alkyl moiety, aryl or oxo.

10. A pharmaceutical composition useful for the treatment of bacterial infections in humans and animals which comprises an antibacterially effective amount of a compound of formula (I) or a pharmaceutically acceptable salt or in vivo hydrolysable ester thereof:

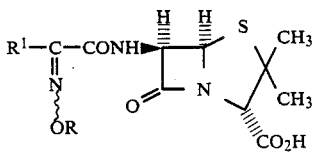

(I)

wherein $R^1$ is a 5 or 6 membered heterocycle containing 1 or 2 nitrogen atoms or 1 or 2 nitrogen atoms and 1 sulphur atom substituted by amino with the proviso, however, that $R^1$ is not 2-amino-thiazol-4-yl; and R is hydrogen; alkyl of 1 to 12 carbon atoms unsubstituted or substituted by carboxyl, esterified carboxyl, carbonyl, hydroxy, alkoxy of 1 to 6 carbon atoms, cyano, carbamoyl, aryloxy, aralkoxy of 1 to 6 carbon atoms in the alkoxy moiety, mercapto, alkylthio of 1 to 6 carbon atoms, arylthio, amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, heterocyclyl or carbo-cyclyl; alkenyl of 2 to 12 carbon atoms unsubstituted or substituted by carboxyl, esterified carboxyl, carbonyl, hydroxy, alkoxy of 1 to 6 carbon atoms, cyano, carbamoyl, aryloxy, aralkoxy of 1 to 6 carbon atoms in the alkoxy moiety, mercapto, alkylthio of 1 to 6 carbon atoms, arylthio, amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, heterocyclyl or carbocyclyl; alkynyl of 2 to 12 carbon atoms unsubstituted or substituted by carboxyl, esterified carboxyl, carbonyl, hydroxy, alkoxy of 1 to 6 carbon atoms, cyano, carbamoyl, aryloxy, aralkoxy of 1 to 6 carbon atoms in the alkoxy moiety, mercapto, alkylthio of 1 to 6 carbon atoms, arylthio, amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, heterocyclyl or carbocyclyl; carbocyclyl of 1 to 4 rings unsubstituted or substituted by alkyl of 1 to 6 carbon atoms, alkenyl of 2 to 6 carbon atoms, alkynyl of 2 to 6 carbon atoms, exo-methylene, carboxyl, alkoxycarbonyl of 1 to 6 carbon atoms in the alkoxy moiety, oxo, hydroxy, alkoxyimino of 1 to 6 carbon atoms, oxyimino, alkoxy of 1 to 6 carbon atoms, cyano, carbamoyl, aryloxy, aralkoxy of 1 to 6 carbon atoms in the alkoxy moiety, mercapto, alkylthio, arylthio, amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, heterocyclyl or carbocyclyl; or heterocyclyl unsubstituted or substituted by halo, alkyl, of 1 to 6 carbon atoms, carbocyclyl, alkylthio, acylamino, alkoxy of 1 to 6 carbon atoms, haloalkyl of 1 to 6 carbon atoms, hydroxy, amino, carboxy, carbamoyl, acyl, alkoxycarbonyl of 1 to 6 carbon atoms in the alkoxy moeity, alkoxycarbonylalkyl of 1 to 6 carbon atoms in the alkoxycarbonyl moiety and 1 to 6 carbon atoms in the alkyl moiety, aryl or oxo, in combination with a pharmaceutically acceptable carriers.

11. A composition according to claim 10, wherein $R^1$ is a member selected from the group consisting of aminopyridyl, amino-pyrimidyl and aminothiadiazole.

12. A composition according to claim 10, wherein R is partly saturated carbocyclyl.

13. A composition according to claim 10, wherein R is alkyl, alkenyl or alkynyl of 3 to 6 carbon atoms having a secondary or tertiary carbon atom at the point of attachment to the oxyimino moiety.

14. A composition according to claim 10, wherein R is cyclopenyl, cyclohexyl, or t-butyl.

15. A composition according to claim 10, wherein the compound is the syn-isomer of formula (II):

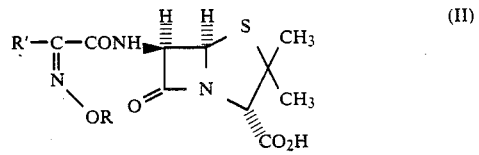

(II)

or a pharmaceutically acceptable salt or in vivo hydroylsable ester thereof.

16. A composition according to claim 15, wherein R is cyclohexyl.

17. A composition according to claim 10, wherein the compound is a member selected from the group consisting of 6β-[2-aminopyridol-6-yl)-(Z)-2-cyclohexyloxyiminoacetamido]penicillanic acid, 6β-[2-(4-aminopyrimid-2-yl)-2-(Z)-cyclohexyloxyiminoacetamido]penicillanic acid, or 6β-[2-(5-amino 1,2,4 thiadiazol-3-yl)-2-(Z)-2-cyclohexyloxyiminoacetamido]penicillanic acid.

18. A method of treating bacterial infections in humans and animals, which comprises administering to a human or animal in need thereof an antibacterially effective amount of a compound of formula (I) or a pharmaceutically acceptable salt or in vivo hydroylsable ester thereof:

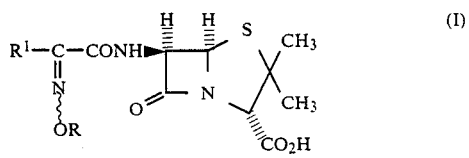

(I)

wherein R¹ is a 5 or 6 membered heterocycle containing 1 or 2 nitrogen atoms or 1 or 2 nitrogen atoms and 1 sulphur atom substituted by amino with the proviso, however, that R¹ is not 2-amino-thiazol-4-yl; and R is hydrogen; alkyl of 1 to 12 carbon atoms unsubstituted or substituted by carboxyl, esterfied carboxyl, carbonyl, hydroxy, alkoxy of 1 to 6 carbon atoms, cyano, carbamoyl, aryloxy, aralkoxy of 1 to 6 carbon atoms in the alkoxy moiety, mercapto, alkylthio of 1 to 6 carbon atoms, arylthio, amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, heterocyclyl or carbocyclyl; alkenyl of 1 to 12 carbon atoms unsubstituted ro substituted by carboxyl, esterfied carboxyl, carbonyl, hydroxy, alkoxy of 1 to 6 carbon atoms, cyano, carbamoyl, aryloxy, aralkoxy of 1 to 6 carbon atoms in the alkoxy moiety, mercapto, alkylthio of 1 to 6 carbon atoms, arylthio, amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, heterocyclyl or carbocyclyl; alkynyl of 2 to 12 carbon atoms unsubstituted or substituted by carboxyl, esterfied carboxyl, carbonyl, hydroxy, alkoxy of 1 to 6 carbon atoms, cyano, carbamoyl, aryloxy, aralkoxy of 1 to 6 carbon atoms in the alkoxy moiety, mercapto, alkylthio of 1 to 6 carbon atoms, arylthio, amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, heterocyclyl or carbocyclyl; carbocyclyl of 1 to 4 rings unsubstituted or unsubstituted by alkyl of 1 to 6 carbon atoms, alkenyl of 2 to 6 carbon atoms, alkynyl of 2 to 6 carbon atoms, exo-methylene, carboxyl, alkoxycarbonyl of 1 to 6 carbon atoms in the alkoxy moiety, oxo, hydroxy, alkoxyamino of 1 to 6 carbon atoms, oxyimino, alkoxy of 1 to 6 carbon atoms, cyano, carbamoyl, aryloxy, aralkoxy of 1 to 6 carbon atoms in the alkoxy moiety, mercapto, alkylthio, arylthio, amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, heterocyclyl or carbocyclyl; or heterocyclyl unsubstituted or substituted by halo, alkyl of 1 to 6 carbon atoms, carbocyclyl, alkylthio, acylamino, alkoxy of 1 to 6 carbon atoms, haloalkyl of 1 to 6 carbon atoms, hydroxy, amino, carboxy, carbamoyl, acyl, alkoxycarbonyl of 1 to 6 carbon atoms in the alkoxy moiety, alkoxycarbonylalkyl of 1 to 6 carbon atoms in the alkoxy moiety and 1 to 6 carbon atoms in the alkyl moiety, aryl or oxo, in combination with a pharmaceuitcal carrier.

19. A method according to claim 18, wherein R¹ is a member selected from the group consisting of aminopyridyl, aminopyrimidyl and aminothiadiazole.

20. A method according to claim 18, wherein R is partly saturated carbocyclyl.

21. A method according to claim 18, wherein R is alkyl, alkenyl or alkynyl of 3 to 6 carbon atoms having a secondary or tertiary carbon atom at the point of attachment to the oxyimino moiety.

22. A method according to claim 18, wherein R is cyclopentyl, cyclohexyl, or t-butyl.

23. A method according to claim 18, wherein the compound is the syn-isomer of formula (II):

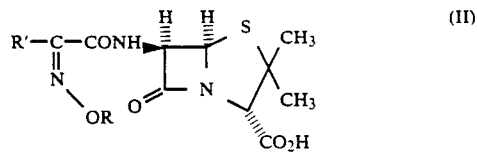

or a pharmaceutically acceptable salt or in vivo hydrolysable ester.

24. A method according to claim 23, wherein R is cyclohexyl.

25. A method according to claim 18, wherein the compound is a member selected from the group consisting of 6β-[2-aminopyridol-6-yl)-(Z)-2-cyclohexyloxyiminoacetamido]penicillanic acid, 6β-[2-(4-aminopyrimid-2-yl)-2-(Z)-cyclohexyloxyiminoacetamido]penicillanic acid, or 6β-[2-(5-amino 1,2,4 thiadiazol-3-yl)-2-(Z)-2-cyclohexyloxyiminoacetamido]penicillanic acid.

* * * * *